United States Patent [19]

Kline

[11] 4,284,823

[45] Aug. 18, 1981

[54] PROCESS FOR PREPARING 3-(3,5-DI-TERT.ALKYL-4-HYDROXY-PHENYL)-2,2-DI-SUBSTITUTED PROPIONALDEHYDES

[75] Inventor: Richard H. Kline, Silver Lake, Ohio

[73] Assignee: The Goodyear Tire & Rubber Company, Akron, Ohio

[21] Appl. No.: 84,490

[22] Filed: Oct. 15, 1979

[51] Int. Cl.³ ............................................. C07C 45/61
[52] U.S. Cl. .................................. 568/433; 568/315; 568/706; 568/707
[58] Field of Search ..................... 260/600 R; 568/433

[56] References Cited

U.S. PATENT DOCUMENTS 4,091,225  5/1978  Parker ............................. 260/600 R

*Primary Examiner*—Bernard Helfin
*Attorney, Agent, or Firm*—D. O. Nickey

[57] ABSTRACT

There is disclosed a process comprising reacting a compound having the general structural Formula II:

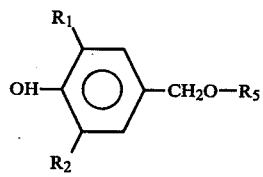

with a compound having the general Formula III:

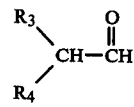

in the presence of a basic catalyst while dissolved in an organic solvent to yield an aldehyde having the structural Formula I:

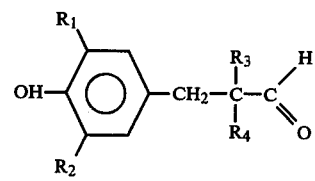

wherein $R_1$ and $R_2$ are the same or different radicals selected from the group consisting of tertiary alkyl radicals having from 4 to 12 carbon atoms, $R_3$ and $R_4$ are the same or different radicals selected from the group consisting of alkyl radicals containing from 1 to 12 carbon atoms, cycloalkyl radicals containing from 5 to 12 carbon atoms, phenyl and substituted phenyl radicals or $R_3$ and $R_4$ with the carbon atom to which they are joined may form a cycloalkyl ring of from 5 to 12 carbon atoms, $R_5$ is selected from the group consisting of hydrogen, alkyl radicals containing from 1 to 12 carbon atoms, or a cycloalkyl radical containing 5 or 6 carbon atoms.

7 Claims, No Drawings

PROCESS FOR PREPARING 3-(3,5-DI-TERT.ALKYL-4-HYDROXY-PHENYL)-2,2-DI-SUBSTITUTED PROPIONALDEHYDES

TECHNICAL FIELD

This invention relates to a novel and useful process for the preparation of certain 3-(3,5-di-tert.alkyl-4-hydroxyphenyl)-2,2-di-substituted propionaldehydes, hereinafter known as 3HP compounds. In particular, the invention concerns the preparation of the compounds of Formula I:

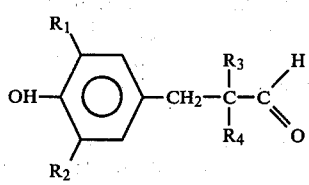

wherein $R_1$ and $R_2$ represent tertiary alkyl radicals containing 4 to 8 carbon atoms and wherein $R_3$ and $R_4$ are selected from the group comprised of alkyl radicals containing from 1 to 12 carbon atoms, cycloalkyl radicals containing from 5 to 12 carbon atoms, phenyl, substituted phenyl radicals, or $R_3$ and $R_4$ together with the carbon atom to which they are joined form a cycloalkyl ring of from 5 to 12 carbon atoms.

BACKGROUND ART

The 3HP compounds of Formula I are useful as stabilizers in organic material normally subject to deterioration caused by heat, light and oxygen. In addition to being antioxidants they are even more useful as intermediates for the preparation of high molecular weight antioxidants for polypropylene and other substrates.

Other methods for the preparation of the aldehydes obtained from the process of this invention are described in British Patent No. 1,455,766 and in U.S. Pat. No. 4,091,225. Both the British and the U.S. Patents claim a process in which 3,5-di-tert.butyl-4-hydroxybenzyl chloride is reacted with isobutyraldehyde under phase transfer conditions. The British Patent describes the product as a red-brown oil, however, the process disclosed in the U.S. Pat. avoids discloration of the product by carrying out the process under an atmosphere of nitrogen.

A difficulty with use of benzyl chloride as taught in the prior art is that a possible coproduct in the preparation of the benzyl chloride is bis(chloromethyl) ether, which is known to be carcinogenic. Thus, it is highly desirable to find other compounds and processes which are capable of forming the desired aldehyde without the use of the benzyl chloride.

The process of the present invention is superior to these in that it produces a light yellow solid product even when carried out in an atmosphere of air. In addition, the art described in the references requires that a mixture of the reactants be added slowly (greater than 2 hours) to the reaction medium. In the process of the present invention it is preferred that the aldehyde not be added until the reaction mixture has been heated to the desired temperature; then the aldehyde may be added in a rapid manner, (10 to 15 minutes), not as taught and disclosed in the prior art references. It has been determined that the aldehyde may in fact be added all at once without having any appreciable effect on either the yield or purity of the desired product.

British Pat. No. 1,455,766 also claims a process in which a 3,5-di-tert.butyl-4-hydroxybenzyl-N,N-dialkyl-dithiocarbamate is reacted with isobutyraldehyde. The British process gives a higher yield and a purer product than the other processes described. However, the yield is still not as high as that obtained from the process of the present invention.

Another advantage of the process of the present invention over the prior art is that it does not require the use of highly flammable carbon disulfide, one of the reactants needed to form the dithiocarbamate in the above-referenced patent.

The only known reference to 2,6-di-tert.butyl-4-alkoxymethylphenyl in the alkylation of an active hydrogen compound is U.S. Pat. No. 4,014,943. In this patent the compound alkylated is nitromethane and the yield of the product after removing insoluble material is only 65%. U.S. Pat. No. 4,014,943 also teaches the use of equimolar amounts of base and nitro compounds while the process of the present invention can be carried out using as little as 3 mole percent of base.

It is the novel and useful process for the preparation of 3HP compounds using 2,6-di-tert.butyl-4-methoxymethylphenol as a highly effective alkylating agent for aldehydes which have only one hydrogen on the carbon adjacent to the carbonyl group that forms the basis of this invention. The product yields using the processes of this invention are greater than 95% in all cases and the purity of the desired product is high.

DISCLOSURE OF THE INVENTION

The process of this invention comprises reacting a compound of Formula II:

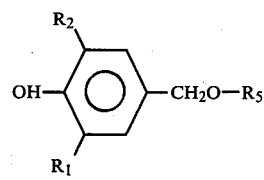

with a further compound of Formula III:

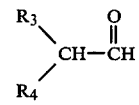

to yield a product of general structural Formula I:

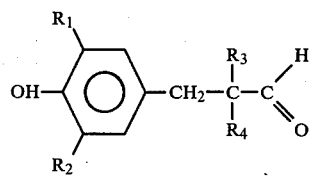

wherein $R_1$ and $R_2$ represent tertiary alkyl radicals containing 4 to 8 carbon atoms. $R_5$ is selected from the group consisting of hydrogen, alkyl radicals containing from 1 to 12 carbon atoms, or cycloalkyl radicals containing from 5 to 6 carbon atoms; and $R_3$ and $R_4$ are selected from the group consisting of alkyl radicals containing from 1 to 12 carbon atoms, cycloalkyl radicals containing from 5 to 12 carbon atoms, phenyl and substituted phenyl radicals, or $R_3$ and $R_4$ together with the carbon atom to which they are joined form a cycloalkyl ring of from 5 to 12 carbon atoms.

DETAILED DESCRIPTION

The reaction is carried out in solvents such as aliphatic alcohols which are water soluble, such as methanol, ethanol and 2-propanol, and aliphatic ethers such as tetrahydrofuran and aliphatic nitriles such as acetonitrile.

The reaction is carried out at a temperature from 20° C. to the boiling point of the solvent. Preferably the reaction is conducted at solvent reflux temperature.

Suitable catalysts for the reaction are the alkali hydroxides and alkoxides such as sodium hydroxide, sodium methoxide, potassium hydroxide and potassium tert.butoxide. The amount of base catalyst used in the reactions of this invention may range from 2.5 to 100 mole percent relative to the phenol, although from 5 to 15 mole percent is the preferred range.

The highest yield of product is obtained using from 5 to 25 percent excess of the aldehyde to the alkoxymethylphenol.

Representative examples of the compounds of Formula II which are useful in the present invention are the following: 3,5-di-tert.butyl-4-hydroxybenzyl alcohol, 2,6-di-tert.butyl-4-methoxymethylphenol, 2,6-di-tert.butyl-4-isopropoxymethylphenol, 2,6-di-tert.butyl-4-ethoxymethylphenol, 2,6-di-tert.-hexyl-4-methoxymethylphenol, 2,6-di-tert.pentyl-4-hydroxy-methylphenol, 2,6-di-tert.butyl-4-butoxymethylphenol, 2,6-di-tert.butyl-4-hexyloxymethylphenol and 2,6-di-tert.butyl-4-octyloxymethylphenol.

Compounds of Formula III are prepared by well-known reactions and they are also available commercially. Representative of compounds of Formula III which are useful in the present invention are the following: isobutyraldehyde, 2-ethylbutyraldehyde, 2-ethylhexanal and cyclohexanecarboxaldehyde.

The process of this invention can be generally described as heating a solution of a compound of Formula II, and a compound of Formula III and a base under reflux for from 2 to 6 hours. The base is then neutralized and the reaction mixture is poured into water. Solid products are isolated by filtration and liquid products by extraction followed by evaporation. The invention is further illustrated by reference to the following examples, which are intended to be representative rather than restrictive of the scope of this invention.

BEST MODE FOR CARRYING OUT THE INVENTION

Example 1

A solution of 25 grams (0.1 mole) of 2,6-di-tert.butyl-4-methoxymethylphenol and one gram (0.015 mole) of KOH in 100 milliliters of methanol was heated to 60° C. 9 grams (0.125 moles) of isobutyraldehyde was added to the solution during a period of 10 minutes and the reaction mixture was heated under reflux for 3 hours. After the mixture had cooled to room temperature it was poured into 125 milliliters of 1% acetic acid. The solid that precipitated was filtered off and allowed to dry. There was obtained 28.5 grams (98.2% of theory) of 2,2-dimethyl-3-(3,5-di-tert.butyl-4-hydroxyphenyl) propionaldehyde with a melting point of 72° to 74° C.

Effect of the solvent and base used in Example 1, (The reaction of 2,6-di-tert.butyl-4-methoxymethyl phenol with isobutyraldehyde) was examined with the results shown in Table 1:

TABLE I

Effect of Solvent and Base in Example 1

| Example | Solvent | Base (1 gram) | % Yield | M.P. (°C.) |
|---|---|---|---|---|
| 1 | Methanol | KOH | 98.2 | 72–74 |
| 2 | Methanol | KOH(0.2 gm.) | 98.8 | 68–71 |
| 3 | Methanol | NaOH | 99.0 | 63–67 |
| 4 | Methanol | NaOCH₃ | 99.6 | 66–69 |
| 5 | Tetrahydrofuran | KOC(CH₃)₃ | 100 | 61–67 |
| 6 | Acetonitrile | KOC(CH₃)₃ | 97.0 | 68–70 |

The results, as shown in Table I, indicate that only a small amount of potassium hydroxide is required for this reaction to take place. The table also shows that the reaction can be run in ethers and nitriles, at least when potassium tert.butoxide is used as the base, with only a slight decrease in product purity. In addition, the examples 3 and 4 indicate that sodium hydroxide and methoxide catalyze the reaction as well as the potassium bases do.

Other aldehydes have been substituted in the process described in Example 1 for isobutyraldehyde. The results are shown in Table II below wherein x will hereinafter denote a tert.butyl radical.

TABLE II $$OH-\underset{X}{\overset{X}{\bigcirc}}-CH_2OCH_3 + \underset{R_4}{\overset{R_3}{>}}CHCHO \longrightarrow$$

$$OH-\underset{X}{\overset{X}{\bigcirc}}-CH_2-\underset{R_4}{\overset{R_3}{\underset{|}{C}}}-CHO$$

| | R₃ | R₄ | Yield (% of theory) | M.P. |
|---|---|---|---|---|
| Example 7 | C₂H₅ | C₂H₅ | 99.4 | 58.2–61° C. |
| Example 8 | C₃H₇ | CH₃ | 97.5 | liquid |
| Example 9 | cyclohexyl* | cyclohexyl* | 97.2 | 71–75° C. |

*R₃ and R₄ together with the carbon atom to which they are joined form a cyclohexyl ring.

The following Table involves the use of 2,6-di-tert.butyl-4-alkoxymethylphenols other than 2,6-di-tert.butyl-4-methoxymethylphenol as the alkylating agent. The results of this set of examples are shown in Table III. All runs were made in methanol using 1 gram of potassium hydroxide as the base and otherwise following Example 1.

TABLE III $$OH-\underset{X}{\overset{X}{\bigcirc}}-CH_2O-R_5 + \underset{CH_3}{\overset{CH_3}{>}}CHCHO \longrightarrow$$

$$OH-\underset{X}{\overset{X}{\bigcirc}}-CH_2-\underset{CH_3}{\overset{CH_3}{\underset{|}{C}}}-CHO + R_5OH$$

| Example | R₅ | % Yield | M.P. (°C.) |
|---|---|---|---|
| (1) | CH₃ | 98.2 | 72–74 |
| 10 | H | 100 | 68–71 |
| 11 | CH₂CH₂ | 99.0 | 71.5–73 |
| 12 | (CH₃)₂CH | 87.6 | 72–74 |
| 13 | C₈H₁₇ | 76.8 | 63.5–71 |

As shown, high purity products were obtained from all but one of the alkylating agents. The yield and purity of the product obtained from the octyloxymethylphenol (Example 13) could be improved by distilling off the water insoluble co-product, 1-octanol.

In order to illustrate the selective nature of the alkoxymethylphenols to aldehyde activated hydrogen compounds the following experiments set out in Tables IV and V were performed.

The reaction of 2,6-di-tert.butyl-4-methoxymethylphenol with active hydrogen compounds in which the activation is provided by groups other than the aldehyde group was investigated. The active hydrogen compounds used and the results of the alkylations are listed in Tables IV and V below. The methanol/potassium hydroxide system was used in all runs except those in which the active hydrogen compound contained an ester group, in which case, an ethanol/sodium ethoxide system was used to avoid transesterification of the esters. Otherwise, the procedure is as outlined in Example 1.

TABLE IV $$\text{OH} - \underset{X}{\overset{X}{\bigcirc}} - CH_2OCH_3 + \overset{CH_3}{\underset{CH_3}{\diagdown}}CH-X \longrightarrow$$

$$\text{OH} - \underset{X}{\overset{X}{\bigcirc}} - CH_2 - \underset{CH_3}{\overset{CH_3}{\underset{|}{C}}} - X + CH_3OH$$

| Example | X | % Yield | Crude Product M.P. (°C.) | Recrystallized % Yield | Product M.P. (°C.) |
|---------|------|---------|--------------------------|------------------------|--------------------|
| 14 | NO2 | 96.7 | 90–97 | 75.6 | 100–102.5 |
| 15 | COCH3 | 99.4 | 50–64 | 96.7 | 69–74 |
| 16 | CN | No Reaction | — | — | — |
| 17 | COOEt | No Reaction | — | — | — |

Table IV shows that 2,6-di-tert.butyl-4-methoxymethylphenol is a more effective alkylating agent for the aldehydes in Table II than for any other type of active hydrogen compound.

Substitution of the doubly activated compounds of Table V for the isobutyraldehyde of Example 1 gave the following results:

TABLE V $$\text{OH} - \underset{X}{\overset{X}{\bigcirc}} - CH_2 - OCH_3 + CH_2\overset{X}{\underset{Y}{\diagdown}} \longrightarrow$$

$$\text{OH} - \underset{X}{\overset{X}{\bigcirc}} - CH_2CH\overset{X}{\underset{Y}{\diagdown}} + CH_3OH$$

| Example | X | Y | Product |
|---------|------|------|---------|
| 18 | COCH3 | COCH3 | $\text{OH} - \underset{X}{\overset{X}{\bigcirc}} - CH_2 - CH\overset{COCH_3}{\underset{COCH_3}{\diagdown}} + \text{OH} - \underset{X}{\overset{X}{\bigcirc}} - CH_2CH_2COCH_3$ |
| 19 | COOEt | COOEt | No Reaction |

TABLE V-continued $$\text{OH} - \underset{X}{\overset{X}{\bigcirc}} - CH_2 - OCH_3 + CH_2\overset{X}{\underset{Y}{\diagdown}} \longrightarrow$$

$$\text{OH} - \underset{X}{\overset{X}{\bigcirc}} - CH_2CH\overset{X}{\underset{Y}{\diagdown}} + CH_3OH$$

| Example | X | Y | Product |
|---------|-------|-------|-------------|
| 20 | COOEt | CN | No Reaction |
| 21 | COOEt | COCH3 | No Reaction |
| 22 | CN | CN | No Reaction |

The lack of reactivity of 2,6-di-tert.butyl-4-methoxymethylphenol with the doubly activated compounds of Table 5 is rather surprising since these compounds are readily alkylated by a wide variety of alkylating agents.

INDUSTRIAL APPLICABILITY

From the results obtained in the examples, it is evident that the process of this invention will alleviate the problems of preparing compounds such as 3(3,5-di-ter.t.alkyl-4-hydroxyphenyl)2,2-disubstituted propionaldehydes in that it avoids the necessity of reacting 3,5-di-tert.alkyl-4-hydroxybenzyl chloride in a phase transfer reaction. Also, the use of an inert atmosphere as disclosed in the prior art is obviated. In addition, a very beneficial aspect of this invention is the unusually high yield and high purity of the desired product. The process of the present invention is superior to those of the past in that the process of this invention produces a light yellow solid product wherein the processes described in the references provide products of inferior purity and yield. In addition, the process of this invention has greatly lessened the preparation time of the desired product. Another advantage of the process of the present invention is that it does not require the use of highly flammable carbon disulfide as taught in the prior art. The products of this process invention are useful as antioxidants for organic materials, but more importantly as intermediates for the preparation of high molecular weight polypropylene antioxidants.

While certain representative embodiments and details have been shown for the purpose of illustrating the invention, it will be apparent to those skilled in this art that various changes and modifications may be made therein without departing from the spirit or scope of the invention.

I claim:

1. A process comprising reacting a compound having the general structural Formula II:

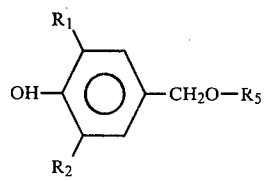

II with a compound having the general Formula III:

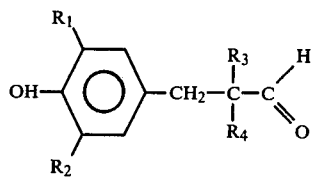

in the presence of a catalyst selected from the group consisting of alkali metal hydroxides and alkali metal alkoxides while dissolved in an organic solvent selected from the group consisting of aliphatic alcohols, aliphatic ethers and aliphatic nitriles to yield an aldehyde having the structural Formula I:

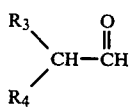

wherein $R_1$ and $R_2$ are the same or different radicals selected from the group consisting of tertiary alkyl radicals having from 4 to 12 carbon atoms, $R_3$ and $R_4$ are the same or different radicals selected from the group consisting of alkyl radicals containing from 1 to 12 carbon atoms, cycloalkyl radicals containing from 5 to 12 carbon atoms and phenyl radicals or $R_3$ and $R_4$ with the carbon atoms to which they are joined may form a cycloalkyl ring of from 5 to 12 carbon atoms, $R_5$ is selected from the group consisting of hydrogen, alkyl radicals containing from 1 to 12 carbon atoms, or a cycloalkyl radical containing 5 to 6 carbon atoms.

2. A process as described in claim 1 above wherein compounds having the general structural formula II are selected from the group consisting of 2,6-di-tert.butyl-4-methoxymethylphenol, 2,6-di-tert.butyl-4-ethoxymethylphenol and 2,6-di-tert.butyl-4-hydroxymethylphenol.

3. A process as described in claim 1 above wherein compounds having the general formula III are selected from the group consisting of isobutyraldehyde, 2-ethylbutyraldehyde, 2-ethylhexanal and cyclohexanecarboxaldehyde.

4. A process as described in claim 1 wherein the catalyst is selected from the group consisting of sodium hydroxide, sodium ethoxide, sodium methoxide, potassium tert.butoxide, and potassium hydroxide.

5. A process as described in claim 1 wherein the solvent is selected from the group consisting of methanol, ethanol and 2-propanol.

6. A process according to claim 1 wherein the reaction is carried out at a temperature from 20° C. to the reflux temperature of the reaction mixture.

7. A process comprising reacting 2,6-di-tert.butyl-4-methoxymethylphenol or 2,6-di-tert.butyl-4-hydroxymethylphenol with isobutyraldehyde in the presence of potassium hydroxide as a catalyst to yield 3-(3,5-di-tert.butyl-4-hydroxyphenyl)-2,2-dimethylpropionaldehyde.

* * * * *

UNITED STATES PATENT OFFICE
CERTIFICATE OF CORRECTION

PATENT NO. : 4,284,823
DATED : August 18, 1981
INVENTOR(S) : Richard H. Kline

It is certified that error appears in the above—identified patent and that said Letters Patent are hereby corrected as shown below:

at Col. 4, Line 65 -- $CH_2CH_2$ -- should be deleted and " $CH_3CH_2$ " should be inserted therefor.

Signed and Sealed this

Nineteenth Day of January 1982

[SEAL]

Attest:

Attesting Officer

GERALD J. MOSSINGHOFF

Commissioner of Patents and Trademarks